US011622676B2

(12) United States Patent
Zhang

(10) Patent No.: US 11,622,676 B2
(45) Date of Patent: Apr. 11, 2023

(54) METHOD OF EXAMINING DIGESTIVE TRACT IMAGES, METHOD OF EXAMINING CLEANLINESS OF DIGESTIVE TRACT, AND COMPUTER DEVICE AND READABLE STORAGE MEDIUM THEREOF

(71) Applicant: ANKON TECHNOLOGIES CO., LTD, Wuhan (CN)

(72) Inventor: Hang Zhang, Wuhan (CN)

(73) Assignee: ANKON TECHNOLOGIES CO., LTD., Wuhan (CN)

( * ) Notice: Subject to any disclaimer, the term of this patent is extended or adjusted under 35 U.S.C. 154(b) by 358 days.

(21) Appl. No.: 17/011,343

(22) Filed: Sep. 3, 2020

(65) Prior Publication Data
US 2021/0059510 A1    Mar. 4, 2021

(30) Foreign Application Priority Data
Sep. 3, 2019  (CN) .......................... 201910825798.6

(51) Int. Cl.
*A61B 1/04*   (2006.01)
*A61B 1/273*  (2006.01)
(Continued)

(52) U.S. Cl.
CPC .......... *A61B 1/041* (2013.01); *A61B 1/00009* (2013.01); *A61B 1/273* (2013.01);
(Continued)

(58) Field of Classification Search
CPC ........... A61B 1/04; A61B 1/041; A61B 1/043; A61B 1/044; A61B 1/00002; A61B 1/00071; A61B 1/00112; A61B 1/00131; A61B 1/00009; A61B 1/000094; A61B 1/000095; A61B 1/000096; A61B 1/273;
(Continued)

(56) References Cited

U.S. PATENT DOCUMENTS

| 8,553,953 | B2 * | 10/2013 | Lee ................... A61B 1/000094 |
| | | | 382/128 |
| 2009/0051695 | A1 * | 2/2009 | Matsuda ............... G06T 7/0012 |
| | | | 345/556 |

(Continued)

FOREIGN PATENT DOCUMENTS

| CN | 103093180 A | 5/2013 |
| CN | 104658014 A | 5/2015 |

*Primary Examiner* — Edward F Urban
*Assistant Examiner* — Duy Tran
(74) *Attorney, Agent, or Firm* — Treasure IP Group, LLC

(57) ABSTRACT

A method of examining digestive tract images is provided. The method of examining digestive tract images include: obtaining a basic image taken by a photographing apparatus; obtaining a set H of pixels with Hue in the range of D1 in the basic image; obtaining a set S of pixels with Saturation in the range of D2 in the basic image; obtaining a set of pixels with Value in the range of D3 in the basic image, and recording it as an effective pixel range; selecting all pixel sets of the set H and the set S in the effective pixel range to form a detection graph block; examining whether the basic image is an unclean image according to the detection graph block. The present invention further provides a method of examining the cleanliness of the digestive tract, a computer device, a computer-readable storage medium thereof.

12 Claims, 1 Drawing Sheet

(51) Int. Cl.
*A61B 1/00* (2006.01)
*G06T 7/00* (2017.01)

(52) U.S. Cl.
CPC ........ *G06T 7/0012* (2013.01); *A61B 1/00016* (2013.01); *G06T 2207/10068* (2013.01); *G06T 2207/30092* (2013.01)

(58) Field of Classification Search
CPC .......... A61B 1/303; A61B 1/307; A61B 1/31; A61B 1/00016; A61B 1/00013; G06T 7/0012; G06T 7/0002; G06T 7/0008; G06T 2207/10068; G06T 2207/30092; G06T 2207/30028; G09G 2300/0439; G09G 2300/0443; G09G 2300/0452; G09G 2300/0456
See application file for complete search history.

(56) References Cited

U.S. PATENT DOCUMENTS

| | | | |
|---|---|---|---|
| 2010/0027858 A1* | 2/2010 | Afik ................... | A61B 5/14539 382/128 |
| 2015/0117729 A1* | 4/2015 | Kim ..................... | G06V 10/273 382/128 |
| 2015/0187063 A1* | 7/2015 | Takahashi .............. | A61B 1/041 382/128 |
| 2015/0193929 A1* | 7/2015 | Ikemoto ........... | A61B 1/000095 382/128 |

* cited by examiner

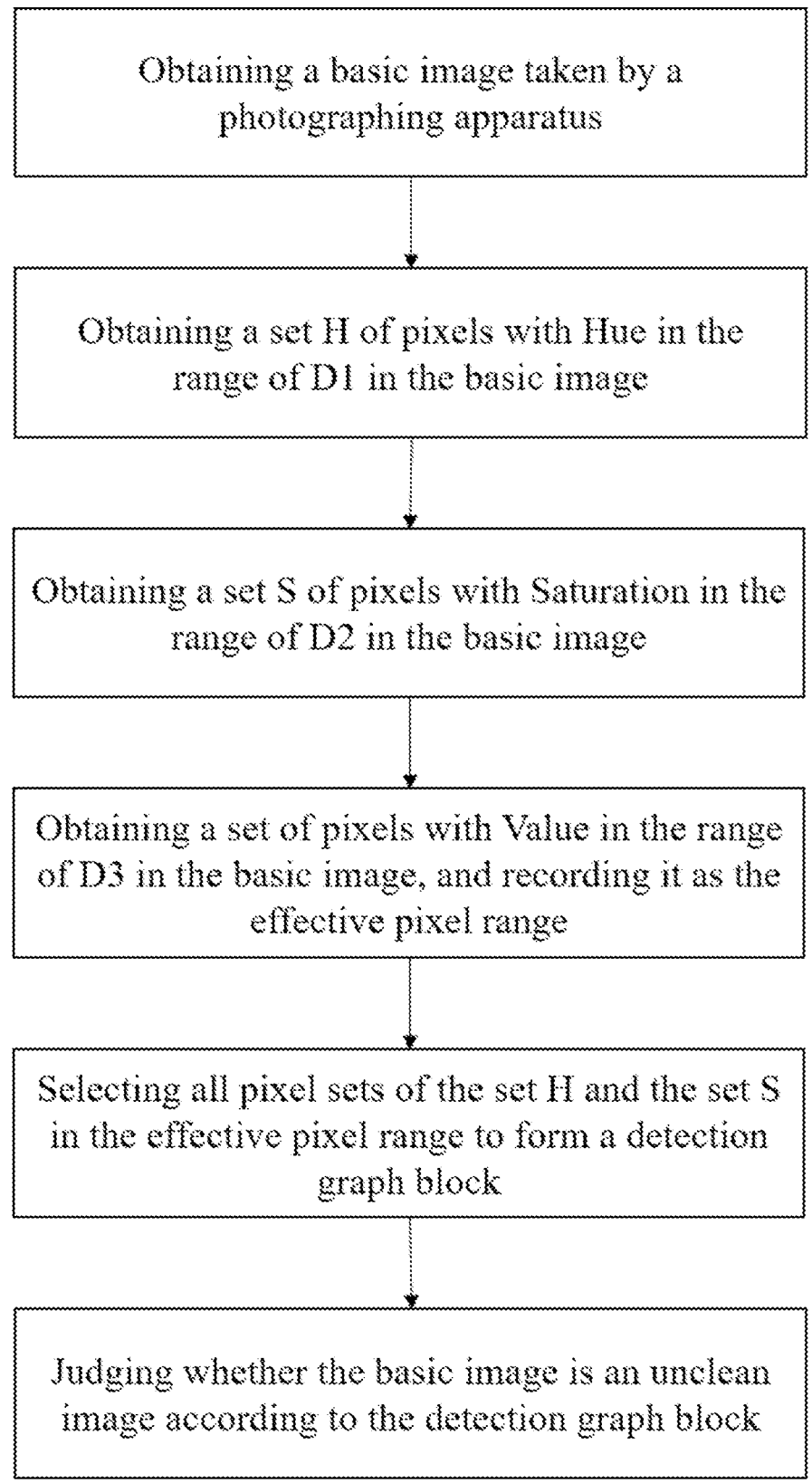

METHOD OF EXAMINING DIGESTIVE TRACT IMAGES, METHOD OF EXAMINING CLEANLINESS OF DIGESTIVE TRACT, AND COMPUTER DEVICE AND READABLE STORAGE MEDIUM THEREOF

CROSS-REFERENCE OF RELATED APPLICATIONS

The application claims priority to Chinese Patent Application No. 201910825798.6 filed on Sep. 3, 2019, the contents of which are incorporated by reference herein.

FIELD OF INVENTION

The present invention relates to a capsule endoscope technique and more particularly to a method of examining digestive tract images, a method of examining the cleanliness of digestive tract, and a computer device and a readable storage medium thereof.

BACKGROUND

Nowadays, capsule endoscopy has become an increasingly popular means for examination of digestive tract. It takes images in the digestive tract of a subject, and enables a doctor to examine the subject more intuitively and conveniently. However, during examination of the digestive tract, especially the stomach, by the capsule endoscopy, if the stomach is poorly cleansed, with large amounts of mucus, bubbles, or turbid gastric juice, for example, the capsule endoscope will capture a large number of images containing mucus, bubbles, or turbid gastric juice, which make a complete examination difficult.

Therefore, it is necessary to design a method of examining digestive tract images and a method of examining the cleanliness of digestive tract for examining whether the digestive tract is clean, as well as a computer device and a readable storage medium thereof.

SUMMARY OF THE INVENTION

To solve the above problems, the present invention provides a method of examining digestive tract images. The method of examining digestive tract images comprises: obtaining a basic image taken by a photographing apparatus; obtaining a set H of pixels with Hue in the range of D1 in the basic image; obtaining a set S of pixels with Saturation in the range of D2 in the basic image; obtaining a set of pixels with Value (also Lightness) in the range of D3 in the basic image, and recording it as an effective pixel range; selecting all pixel sets of the set H and the set S in the effective pixel range to form a detection graph block; and examining whether the basic image is an unclean image according to the detection graph block.

Further, D1 ranges from 0 to 40, D2 ranges from 0 to 60, and D3 ranges from 20 to 170.

Further, the step of "examining whether the basic image is an unclean image according to the detection graph block" comprises: calculating the number num of connected components of the detection graph block; when num>T1, determining that the basic image is an unclean image.

Further, the step of "examining whether the basic image is an unclean image according to the detection graph block" comprises: calculating the number num of connected components of the detection graph block; calculating the ratio R1 between the area of the effective pixel range and the total area of the basic image; when num>T1 and R1>T2, determining that the basic image is an unclean image.

Further, the method of examining digestive tract images further comprises: when num≤T1 or R1≤T2, calculating the ratio R2 between the detection graph block and the total area of the basic image; when R2>T3, determining that the basic image is an unclean image.

Further, the value of T2 is between 0.5-0.9.

Further, the connected component is calculated through 4-adjacence, and the value of T1 is between 15-35.

Further, the step of "examining whether the basic image is an unclean image according to the detection graph block" comprises: calculating the ratio R2 between the area of the detection graph block and the total area of the basic image; when R2>T3, determining that the basic image is an unclean image.

Further, the value of T3 is between 0.3-0.7.

To solve the above problems, the present invention provides a method of examining the cleanliness of the digestive tract. The method of examining the cleanliness of the digestive tract comprises: obtaining N1 basic images taken by a photographing apparatus in the digestive tract; obtaining a set H of pixels with Hue in the range of D1 in the basic images; obtaining a set S of pixels with Saturation in the range of D2 in the basic images; obtaining a set of pixels with Value in the range of D3 in the basic images, and recording it as an effective pixel range; selecting all pixel sets of the set H and the set S in the effective pixel range to form detection graph blocks; examining whether the basic images are unclean images according to the detection graph blocks; counting the number of images determined to be unclean as N2; calculating the ratio Ratio of N2 and N1; and when Ratio≥T4, examining that the cleanliness of the digestive tract is poor.

Further, the value of T4 is between 0.3-0.5.

To solve the above problems, the present invention provides a computer device. The computer device, comprises a memory and a processor, where the memory stores computer programs, and the processor executes the computer programs to implement the steps of the method of examining the cleanliness of the digestive tract as described above.

To solve the above problems, the present invention provides a computer-readable storage medium, which storing computer programs. The computer programs can be executed by a processor to implement the steps of the method of examining the cleanliness of the digestive tract as described above.

Compared with the prior art, the present invention using Hue and Saturation to confirm and distinguish the detection graph blocks in the basic images. The detection graph blocks can reflect the unclean parts in the stomach including bubbles, mucus, etc., or clean parts in the stomach. Therefore, it can be determined whether the basic images are unclean images based on the detection graph blocks. Therefore, the user can determine the cleanliness of the digestive tract according to the basic images taken by a capsule endoscope, and determine whether it is necessary to clean the digestive tract before examination.

BRIEF DESCRIPTION OF THE DRAWINGS

FIG. 1 shows a flowchart of a method of examining digestive tract images according to the present invention.

DETAILED DESCRIPTION

In order to enable those skilled in the art to better understand the technical solutions disclosed, the present invention will be described in detail below with reference to the accompanying drawings and preferred embodiments. However, the embodiments are not intended to limit the invention, and obviously, the described embodiments are only a part of the embodiments of the present invention, but not all of them. Based on the embodiments of the present invention, all other embodiments obtained by those having ordinary skill in the art without creative work are included in the protection scope of the present invention.

As shown in FIG. 1, the present invention provides a method of examining digestive tract images. In a specific embodiment of the present invention, a photographing apparatus can be a capsule endoscope, which can be swallowed into the digestive tract and moves forward with the peristalsis of the digestive tract. In addition, the capsule endoscope can be wirelessly connected to an external signal receiving device, and the images taken by the capsule endoscope can be wirelessly transmitted to the signal receiving device and displayed on a display screen to facilitate users to view and determine.

In addition, it should be noted that, in a specific embodiment of the present invention, the digestive tract can be the stomach. Since mucus, bubbles, turbid gastric juice, etc. may be present in the stomach, detailed examination becomes difficult. Therefore, the method of examining the cleanliness of the digestive tract disclosed herein is usually applied to the stomach. The present invention is not only limited to the stomach, but can also be applied to other parts of the digestive tract to determine the cleanliness thereof.

Specifically, the method of examining digestive tract images comprises:

obtaining a basic image taken by a photographing apparatus;

obtaining a set H of pixels with Hue in the range of D1 in the basic image;

obtaining a set S of pixels with Saturation in the range of D2 in the basic image;

obtaining a set of pixels with Value in the range of D3 in the basic image, and recording it as an effective pixel range;

selecting all pixel sets of the set H and the set S in the effective pixel range to form a detection graph block;

examining whether the basic image is an unclean image according to the detection graph block. In this embodiment, the unclean image indicates the presence of mucus, bubbles, turbid gastric juice, etc. in the stomach.

In the scope of the present invention, an unclean image means an image contain an unclean item, which is manifested as mucus, bubbles, or impurities on the image. Such images make it impossible to accurately determine the state of the digestive tract through the image.

Thus, through the steps described above, the sets of pixels with appropriate Hue and Saturation are first obtained in the basic image, and then the effective pixel range is obtained by Value, which are superimposed to form the detection graph block. According to the detection graph block, it can be determined whether the basic image is a clean image. If the effective pixel range is determined first, and then the set H and the set S are selected, the objective of the present invention can also be achieved.

Usually, the environment in the stomach is reddish, so the color of bubbles, mucus, etc. in the stomach can differ in color from the normal environment in the stomach. Therefore, the basic image taken by the photographing apparatus, i.e. the capsule endoscope can also present a significant difference. Therefore, in the present invention, the effective pixel range that can be used for detection is first confirmed by Value, and then the detection graph block in the basic image is confirmed and distinguished by Hue and Saturation. The detection graph block can reflect the unclean parts in the stomach including bubbles, mucus, etc., or clean parts in the stomach, so that it can be determined whether the basic image is an unclean image based on the detection graph block.

Specifically, in an embodiment of the present invention, the detection graph block is a collection of unclean parts in the basic image. In order to obtain the Hue and Saturation of the basic image, the basic image must first be converted into an HSV format. In addition, a set H of pixels with Hue in the range of D1 and a set S of pixels with Saturation in the range of D2 are obtained in the basic image in the HSV format. The D1 ranges from 0 to 40, and the D2 ranges from 0 to 60. Specifically, since the value of Hue ranges from 0 to 360, and the value of Saturation ranges from 0 to 100, after comparison, measurement and calculation, the set of pixels with Hue of 0-40 and Saturation of 0-60 can best represent the positions of the unclean parts in the basic image captured by the photographing apparatus.

Specifically, in the first embodiment of the present invention, the step of "examining whether the basic image is an unclean image according to the detection graph block" comprises:

calculating the number num of connected components of the detection graph block;

when num>T1, determining that the basic image is an unclean image.

Specifically, in this embodiment of the present invention, a connected component analysis is used to determine the number of unclean parts. When the number is greater than a threshold T1, it can be determined that the basic image is an unclean image. According to the unclean image, the corresponding unclean part in the digestive tract can be defoamed by simethicone or other methods to prevent impact on subsequent detection of lesions or other procedures.

In addition, it should be noted that the connected component is usually calculated by a method of 4-adjacence or a method of 8-adjacence. First, a pixel is specified as a basic pixel. The 4-adjacence refers to the adjacent pixels in the up, down, left and right directions of the basic pixel, which can be determined to be adjacent to the basic pixel and form a 4-connected component. The 8-adjacence refers to the adjacent pixels in the up, down, left, right, upper left, lower left, upper right and lower right directions of the basic pixel, which can be determined to be adjacent to the basic pixel and form a 8-connected component. Thus, it can be seen that for the same basic image, the size of the connected component in the 8-adjacence calculation method is usually greater than that in the 4-adjacence calculation method. Correspondingly, the number of the connected components in the 8-adjacence calculation method is smaller than that in the 4-adjacence calculation method.

In the embodiment of the present invention, the connected component is calculated through 4-adjacence calculation method, and the value of T1 is within the range of 15 to 35. Specifically, in this embodiment, the value of threshold T1 is 25. If the connected component is calculated through 8-adjacence or other calculation methods, the value of the threshold T1 can also change accordingly.

In a second embodiment of the present invention, the step of "examining whether the basic image is an unclean image according to the detection graph block" comprises:

calculating the number num of connected components of the detection graph block;

calculating the ratio R1 between the area of the effective pixel range and the total area of the basic image;

when num>T1 and R1>T2, determining that the basic image is an unclean image.

This embodiment is similar to the first embodiment described above. However, generally, if only the parameter num, the number of connected components, is used, the judgment may be inaccurate. Therefore, the second parameter is introduced in this embodiment: calculating the ratio R1 between the area of the effective pixel range and the total area of the basic image. When the number num of connected components is greater than T1, and the ratio R1 is greater than T2, the basic image is determined to be an unclean image. Compared with the first judgment method, this judgment method uses the second parameter to make the judgment more accurate.

Further, the method of examining digestive tract images further comprises:

When num≤T1 or R1≤T2, calculating the ratio R2 between the area of the detection graph block and the total area of the basic image;

when R2>T3, determining that the basic image is an unclean image.

That is, when num>T1 and R1>T2, it can be determined that the basic image is an unclean image. Then, when num≤T1 or R1≤T2, it cannot be directly determined that the basic image is a clean image, but another step of judgment is required. Specifically, the step is calculating the ratio R2 between the area of the detection graph block and the total area of the basic image. Since the detection graph block refers to all the pixel sets including the set H and the set S selected in the effective pixel range, the detection graph block can be a collection of areas in the basic image corresponding to the unclean parts of the digestive tract. Therefore, if the proportion of the detection graph block in the basic image is too large, it can be determined that the basic image is also an unclean image.

Specifically, the value of the threshold T2 ranges from 0.5 to 0.9, and in this embodiment, the value of T2 is 0.7. The value of the threshold T3 ranges from 0.3 to 0.7, and in this embodiment, the value of T3 is 0.5. The value of T1 and the calculation method of the connected component are similar to those in the first embodiment, and cannot be repeated here.

In a third embodiment of the present invention, the step of "examining whether the basic image is an unclean image according to the detection graph block" comprises:

calculating the ratio R2 between the area of the detection graph block and the total area of the basic image;

when R2>T3, determining that the basic image is an unclean image.

Similar to the second embodiment, in this embodiment, instead of pre-calculating the proportion of connected components or effective pixels in the detection graph block, the ratio R2 between the detection graph block and the total area of the basic image is directly calculated for judgment. Specifically, the value of T3 is also the same as that in the second embodiment, and cannot be repeated here.

In addition, in the present invention, as described above, the detection graph block must also be within the range of effective pixels. Therefore, a set of pixels with Value in the range of D3 in the basic image is obtained, and recorded as the effective pixel range. Specifically, in order to distinguish the lightness of the pixels, the basic image can also be converted into a grayscale format, and then make the judgment. In the embodiments of the present invention, the value of D3 ranges from 20 to 170. It is known that the gray value is between 0-255. Therefore, in the embodiments of the present invention, areas with the lightness of too dark or too bright are eliminated, and areas with the lightness of too dark or too bright are not within the effective pixel range in the embodiments.

In addition to using lightness to determine the effective pixel range, in the second embodiment described above, in the process of examining the basic image, the parameter R1, the ratio between the effective pixel range and the total area of the basic image, is introduced as another judgment condition, and the calculation of the effective pixel range is also consistent with the method described above.

The method of examining whether a single basic image in the digestive tract is an unclean image is described above, and the following is a further analysis.

The present invention also introduces a method of examining the cleanliness of the digestive tract based on a photographing apparatus, the method of examining the cleanliness of the digestive tract comprising:

obtaining N1 basic images taken by the photographing apparatus in the digestive tract;

obtaining a set H of pixels with Hue in the range of D1 in the basic images;

obtaining a set S of pixels with Saturation in the range of D2 in the basic images;

obtaining a set of pixels with Value in the range of D3 in the basic images, and recording it as the effective pixel range;

selecting all pixel sets of the set H and the set S in the effective pixel range to form detection graph blocks;

examining whether the basic images are unclean images according to the detection graph blocks;

counting the number of images determined to be unclean as N2;

calculating the ratio Ratio of N2 and N1; and when Ratio≥T4, examining that the cleanliness of the digestive tract is poor.

Compared with the aforementioned method of examining digestive tract images, in this method, N1 basic images are obtained, and the N1 images are determined sequentially or simultaneously for cleanliness. The judgment method is as described above, and cannot be repeated here.

In this method, the ratio Ratio between the number of unclean images and the number of basic images is compared. If the ratio Ratio is too large and exceeds the threshold T4, it indicates that the cleanliness of the digestive tract is poor. When it is determined that the digestive tract, mainly the stomach, is poorly clean, the subject can be allowed to take anti-forming agent, etc. to suppress mucus and bubbles, so as to make subsequent examination more convenient. Specifically, in an embodiment of this method, the value of T4 is in the range of 0.3 to 0.5, and preferably, the value of T4 is 0.4.

The present invention further provides a computer device. The computer device comprises a memory and a processor, where the memory stores computer programs, and the processor executes the computer programs to implement the steps of the method of examining the cleanliness of the digestive tract as described above.

Also, the present invention provides a computer-readable storage medium storing computer program. The computer programs can be executed by the processor to implement the steps of the method of examining the cleanliness of the digestive tract as described above.

In summary, the present invention provides a method of examining digestive tract images, a method of examining the cleanliness of the digestive tract, and a computer device and a readable storage medium thereof. In the method of examining digestive tract images, the range and size of mucus, bubbles, etc. in the digestive tract are determined by examining the range of Hue and Saturation, and then three specific embodiments are used to detail whether the detection graph blocks are unclean images. Moreover, the present invention also introduces lightness to determine the effective pixel range, which makes the judgment of unclean images more accurate. In the method of examining the cleanliness of the digestive tract provided in the present invention, the ratio between the number of the unclean images and the total number of captured images of the digestive tract is used to determine the cleanliness of the digestive tract, mainly the stomach. If the digestive tract is determined to be unclean, the subject can be allowed to take anti-foaming agent, etc. The above method of examining the cleanliness of the digestive tract can also be applied to a computer device and a computer-readable storage medium.

The purpose of this invention is to determine whether the target area is clean through determining if an image is an unclean image. The cleanliness of the digestive tract is determined based on the number of unclean images. Determining whether the digestive tract needs to be cleaned is the ultimate goal of this invention.

It should be understood that, although the specification is described in terms of embodiments, not every embodiment merely includes an independent technical solution. This narration in the specification is for clarity. Those skilled in the art should have the specification as a whole, and the technical solutions in each embodiment may also be combined as appropriate to form other embodiments that can be understood by those skilled in the art.

The series of detailed descriptions listed above are only specific descriptions of the feasible embodiments of the present invention, and are not intended to limit the protection scope of the present invention. Any equivalent embodiments or variations made without departing from the technical spirit of the present invention should be included in the protection scope of the present invention.

The invention claimed is:

1. A method of determining cleanliness of a digestive tract, comprising
    examining digestive tract images to determining cleanliness of images, comprising:
        introducing a capsule endoscope having a photographing apparatus enclosed therein to the digestive tract;
        navigating the capsule endoscope through the digestive tract and taking images of the digestive tract;
        obtaining N1 basic images taken by the photographing apparatus of the capsule endoscope in the digestive tract;
        obtaining a set H of pixels with Hue in the range of D1 in the basic images;
        obtaining a set S of pixels with Saturation in the range of D2 in the basic images;
        obtaining a set of pixels with Value in the range of D3 in the basic image, and recording it as an effective pixel range;
        selecting all pixel sets of the set H and the set S in the effective pixel range to form detection graph blocks;
        examining whether the basic images are unclean images according to the detection graph blocks;
        counting the number of images examined to be unclean as N2;
        calculating the ratio of N2 and N1, noted as Ratio=N2/N1; and
        when Ratio≥T4, T4 is a preset threshold value, determining that the cleanliness of the digestive tract is poor.

2. The method of examining digestive tract images of claim 1, wherein D1 ranges from 0 to 40, D2 ranges from 0 to 60, and D3 ranges from 20 to 170.

3. The method of examining digestive tract images of claim 1, wherein the step of "examining whether the basic image is an unclean image according to the detection graph block" comprises:
    calculating the number num of connected components of the detection graph block;
    when num>T1, determining that the basic image is an unclean image.

4. The method of examining digestive tract images of claim 1, wherein the step of "examining whether the basic image is an unclean image according to the detection graph block" comprises:
    calculating the number num of connected components of the detection graph block;
    calculating the ratio R1 between the area of the effective pixel range and the total area of the basic image;
    when num>T1 and R1>T2, determining that the basic image is an unclean image.

5. The method of examining digestive tract images of claim 4, further comprises:
    when num≤T1 or R1≤T2, calculating the ratio R2 between the area of the detection graph block and the total area of the basic image;
    when R2>T3, determining that the basic image is an unclean image.

6. The method of examining digestive tract images of claim 4, wherein the value of T2 is between 0.5-0.9.

7. The method of examining digestive tract images of claim 3, wherein the connected component is calculated through 4-adjacence, and the value of T1 is between 15-35.

8. The method of examining digestive tract images of claim 1, wherein the step of "examining whether the basic image is an unclean image according to the detection graph block" comprises:
    calculating the ratio R2 between the area of the detection graph block and the total area of the basic image;
    when R2>T3, determining that the basic image is an unclean image.

9. The method of examining digestive tract images of claim 8, wherein the value of T3 is between 0.3-0.7.

10. The method of examining the cleanliness of the digestive tract of claim 1, wherein the value of T4 is between 0.3-0.5.

11. A computer device, comprising a memory and a processor, wherein the memory stores computer programs, and the processor executes the computer programs to implement the steps of a method of examining the cleanliness of digestive tract,
    wherein the method of examining the cleanliness comprises:
        introducing a capsule endoscope having a photographing apparatus enclosed therein to the digestive tract;
        navigating the capsule endoscope through the digestive tract and taking images of the digestive tract;
        obtaining N1 basic images taken by the photographing apparatus in the digestive tract;
        obtaining a set H of pixels with Hue in the range of D1 in the basic images;
        obtaining a set S of pixels with Saturation in the range of D2 in the basic images;
        obtaining a set of pixels with Value in the range of D3 in the basic image, and recording it as an effective pixel range;

selecting all pixel sets of the set H and the set S in the effective pixel range to form detection graph blocks;

examining whether the basic images are unclean images according to the detection graph blocks;

counting the number of images examined to be unclean as N2;

calculating the ratio of N2 and N1, as Ratio=N2/N1; and when Ratio≥T4, wherein T4 is a preset threshold value, examining that the cleanliness of the digestive tract is poor.

12. A non-transitory computer-readable storage medium, which storing computer programs, wherein the computer programs can be executed by a processor to implement the steps of a method of examining the cleanliness of digestive tract, wherein the method of examining the cleanliness comprises:

introducing a capsule endoscope having a photographing apparatus enclosed therein to the digestive tract;

navigating the capsule endoscope through the digestive tract and taking images of the digestive tract;

obtaining N1 basic images taken by the photographing apparatus in the digestive tract;

obtaining a set H of pixels with Hue in the range of D1 in the basic images;

obtaining a set S of pixels with Saturation in the range of D2 in the basic images;

obtaining a set of pixels with Value in the range of D3 in the basic image, and recording it as an effective pixel range;

selecting all pixel sets of the set H and the set S in the effective pixel range to form detection graph blocks;

examining whether the basic images are unclean images according to the detection graph blocks;

counting the number of images examined to be unclean as N2;

calculating the ratio of N2 and N1, as Ratio=N2/N1; and when Ratio>T4, wherein T4 is a preset threshold value, determining that the cleanliness of the digestive tract is poor.

\* \* \* \* \*